United States Patent
Warratz

(10) Patent No.: US 9,395,323 B2
(45) Date of Patent: Jul. 19, 2016

(54) ELECTROCHEMICAL GAS SENSOR WITH AN IONIC LIQUID AS ELECTROLYTE FOR THE DETECTION OF AMMONIA AND AMINES

(71) Applicant: MSA AUER GMBH, Berlin (DE)

(72) Inventor: Ralf Warratz, Bonn (DE)

(73) Assignee: MSA EUROPE GMBH, Jona (CH)

(*) Notice: Subject to any disclaimer, the term of this patent is extended or adjusted under 35 U.S.C. 154(b) by 147 days.

(21) Appl. No.: 14/354,011

(22) PCT Filed: Oct. 25, 2012

(86) PCT No.: PCT/EP2012/071141
§ 371 (c)(1),
(2) Date: Apr. 24, 2014

(87) PCT Pub. No.: WO2013/060773
PCT Pub. Date: May 2, 2013

(65) Prior Publication Data
US 2014/0299470 A1  Oct. 9, 2014

(30) Foreign Application Priority Data

Oct. 25, 2011 (DE) .......... 10 2011 085 174
Dec. 1, 2011 (DE) .......... 10 2011 087 592

(51) Int. Cl.
G01N 27/403 (2006.01)
G01N 27/333 (2006.01)
G01N 27/404 (2006.01)
G01N 33/00 (2006.01)

(52) U.S. Cl.
CPC .......... *G01N 27/333* (2013.01); *G01N 27/4045* (2013.01); *G01N 33/0054* (2013.01)

(58) Field of Classification Search
CPC ................. G01N 27/4045; G01N 33/0054
See application file for complete search history.

(56) References Cited

U.S. PATENT DOCUMENTS

| 4,961,834 A | 10/1990 | Kuhn et al. |
| 6,248,224 B1 | 6/2001 | Kitzelmann |
| 7,060,169 B2 | 6/2006 | Rohrl |
| 7,758,735 B2 | 7/2010 | Hengstenberg et al. |

(Continued)

FOREIGN PATENT DOCUMENTS

| DE | 3841622 C2 | 6/1992 |
| DE | 102005020719 B3 | 9/2006 |

(Continued)

OTHER PUBLICATIONS

Kanzaki et al., Acid-Base Property of Ethylammonium Nitrate Ionic Liquid Directly Obtained Using Ion-selective Field Effect Transistor Electrode, Chemistry Letters vol. 36, No. 5 (2007) pp. 684-685.*

(Continued)

*Primary Examiner* — Alexander Noguerola
(74) *Attorney, Agent, or Firm* — Ference & Associates LLC

(57) ABSTRACT

An electrochemical gas sensor, particularly for the detection of ammonia and/or amines, with an ionic fluid as an electrolyte, wherein the ionic fluid contains at least one protic ammonium cation with at least one dissociable hydrogen atom, whereby the at least one protic ammonium cation reacts with the ammonia and/or amines to be measured via deprotonation. The present invention also relates to the use of such a gas sensor.

24 Claims, 5 Drawing Sheets

(56) References Cited

U.S. PATENT DOCUMENTS

| | | | |
|---|---|---|---|
| 8,623,189 | B2 | 1/2014 | Eckhardt et al. |
| 2006/0249382 | A1 | 11/2006 | Hengstenberg et al. |
| 2011/0226619 | A1 | 9/2011 | Eckhardt et al. |
| 2011/0253534 | A1 | 10/2011 | Eckhardt et al. |

FOREIGN PATENT DOCUMENTS

| | | | |
|---|---|---|---|
| DE | 2010063626 A1 | 6/2010 |
| DE | 102008044238 A1 | 6/2010 |
| DE | 102008044239 A1 | 6/2010 |
| DE | 102008044240 A1 | 6/2010 |
| EP | 1183528 B1 | 12/2010 |
| EP | 1805131 B1 | 2/2011 |
| GB | 2225859 A | 6/1990 |
| WO | 2008110830 A1 | 9/2008 |
| WO | 2013060773 A1 | 5/2013 |

OTHER PUBLICATIONS

A. Safavi et al., "Investigation of the Role of Ionic Liquids in Tuning the pKa Values of Some Anionic Indicators", Journal of Solution Chemistry, vol. 38, No. 6, pp. 753-761, 2009.

MacFarlane et al., "Acids and Bases in Ionic Liquids", Chapter (Book), AGS Symposium Series, vol. 856, Chapter 22, pp. 264-276, 2003.

International Search Authority, Search Report for International Application PCT/EP2012/071141, Jan. 29, 2013 (EPO), 1 page, Rijswijk, NL.

Wei et al, "Applications of ionic liquids in electrochemical sensors", Analytica Chimica ACTA, Dec. 23, 2007, pp. 126-135, vol. 607, No. 2, Elsevier, Amsterdam, NL.

\* cited by examiner

ELECTROCHEMICAL GAS SENSOR WITH AN IONIC LIQUID AS ELECTROLYTE FOR THE DETECTION OF AMMONIA AND AMINES

CLAIM FOR PRIORITY

This application claims priority to German Patent Application Nos. 10 2011 085 174.7 and 10 2011 087 592.1, filed on Oct. 25, 2011 and Dec. 1, 2011, respectively,

TECHNICAL FIELD

The present invention relates to an electrochemical gas sensor.

BACKGROUND

The use of electrochemical sensors for the detection of gaseous components and substances has long been known. Such gas sensors generally include at least two electrodes, in the form of one working electrode and one counter electrode. These electrodes find themselves in mutual contact via a conductor or electrolyte.

Such types of gas sensors and gas cells typically involve one side being open to ambient, e.g., by way of a porous membrane. Gas can flow through such a membrane to the electrodes to be electrochemically converted there. The current resulting from the electrochemical reaction ends up being proportional to the quantity of gas. Various arrangements, represented by sulfuric acid or other aqueous electrolytes, have previously been employed as ionic conductors or electrolytes in such gas sensors.

In recent years, the development of gas sensors has tended towards miniaturization. However, the conventionally employed aqueous electrolytes have not lent themselves to miniaturization because of their strongly hygroscopic properties. These hygroscopic properties of conventional electrolytes ensure that, in a dry environment, dehydration of the gas sensor and gas cell is inhibited. However, in high humidity the electrolyte can take on so much water that the gas cell bursts as a result, and the electrolyte leaks out. To prevent such leakage of electrolytes, it becomes necessary to increase the inner volume of the gas cell to 5 to 7 times the electrolyte fill volume. However, this prevents any meaningful miniaturization of gas cells and gas sensors.

By way of an alternative, electrolytes have manifested as ionic liquids in recent years. Ionic liquids have proven to be unique solvents showing solubility, miscibility and other physiochemical properties (e.g., non-volatile properties) over a broad range.

Ionic liquids are, per definition, liquid salts with a melting point under 100° C. The salt structure of ionic liquids requires a correspondingly negligible vapor pressure. Many ionic liquids are very stable chemically and electrochemically, and feature high conductivity. Some ionic liquids, especially those with hydrophobic cations and/or anions, exhibit relatively low water absorption. At the same time, other ionic liquids show water absorption similarly to an aqueous salt solution. In contrast to aqueous salt solutions, however, these ionic liquids still show an electrical conductivity even at extremely low humidities, while, because of water evaporation, this is not the case for aqueous salts such as LiCl solutions.

During the past decade, the inclusion of ionic liquids in gas sensors was concertedly investigated. As such, the use of gas sensors with ionic liquids used as electrolytes, for the detection of acid gases such as sulfur dioxide or carbon dioxide, has been described (WO 2008/110830 A1, WO 2010/063626 A1).

Different ionic salts with different properties and potential applicability in electrochemical gas sensors were intensively explored. Thus, by way of example, ionic liquids were used based on given cation classes in combination with halide, sulfate, sulfonate, borate, phosphate, antimonate, amide, imide anions. Typical cations are substituted imidazolium ions, pyridinium ions, pyrrolidinium ions, phosphonium ions, ammonium ions and guanidinium ions (DE 10 2005 020 719 B3).

Electrochemical sensors for the detection of ammonia are typically based upon direct oxidation of the gaseous ammonia in the context of molecular nitrogen formation and electron release. However, such sensors exhibit reduced stability, which especially is brought about by exposing the sensor to the ammonia gas for longer time periods.

Another potentiometric measurement principle in ammonia sensors is premised on direct or indirect pH measurement. In such sensors, the ammonia under detection is converted into ammonium ions and hydroxide ions via the water of the electrolyte being employed. This approach is followed, e.g., in EP 1 183 528 B1, in which a sensor for the detection of ammonia and amines is described, incorporating an electrolyte which contains oxidizable $Mn^{2+}$ and a suitable organic solvent. The measurement electrode includes a surface with a catalyst which, in the presence of the gas being measured, catalyzes the oxidation of $Mn^{2+}$ into $Mn^{4+}$. The measurement principle realized here follows this reaction scheme:

$$NH_3 + H_2O \rightarrow NH_4^+ + OH^- \quad (I)$$

$$Mn^{2+} + 2H_2O \rightarrow MnO_2 + 4H^+ + 2e^- \quad (II)$$

The oxidation reaction of the $Mn^{2+}$ is possible because of the pH shift following reaction (I). This pH shift also shifts the redox potential of the Mn2+ oxidation. It has been shown here to be disadvantageous that the $MnO_2$ precipitates from the electrolyte and blocks the measuring electrode and the gas inlet membrane, whereby gas input is reduced significantly. Therefore, such sensors exhibit no type of adequate long-term stability.

Also, the one step that determines reaction speed here is the introduction of equilibrium between electrolyte and gas space. Thus, in addition to low stability, this type of measurement system also has the disadvantage of a relatively long response time with the type of ammonia sensor at hand. As such, a different measurement principle is embraced in DE 38 41 622 C2, whereby the provision of gas sensors for ammonia with relatively short response times is facilitated. In DE 38 41 622 C2, a soluble, non-oxidizable substance is added to the electrolyte, which undergoes a reaction with ammonia during formation of an oxidizable product. In turn, this oxidizable product can be converted into chemically and electrochemically inert byproducts via electrochemical oxidation. Thus, the actual electrochemical reaction is preceded by an equilibrium reaction of ammonia with a non-oxidizable substance, which itself leads to a complete conversion of the ammonia into an easily oxidizable product. Such easily oxidizable products are then oxidized at the measurement electrode. Tris(hydroxymethyl)aminomethanhydrochlorid (Tris-HCl) has proven to be especially suitable for this purpose.

In an acid-base reaction that precedes the actual detection reaction, ammonia diffusing into the gas sensor reacts with the Tris-HCl into an ammonium ion and the corresponding organic amine of Tris-HCl. Further, the organic amine is oxidized electrochemically at the measurement electrode, such that the electrons released at that point contribute to the measurement cell current. The organic amines oxidized at the electrode thence break up into additional reaction products. This measurement principle, by way of example, is set forth in the equations shown in FIG. 1.

And yet, a disadvantage with the described measurement system for ammonia is that the Tris-HCl being used is introduced into a liquid electrolyte. As described hereinabove, the use of aqueous electrolytes does provide a hindrance to the miniaturization of gas sensors as well as performance limitations at low humidity conditions.

SUMMARY

One aspect of the invention provides an electrochemical gas sensor comprising: an electrolyte comprising an ionic liquid; the ionic liquid including at least one protic ammonium cation with at least one dissociable hydrogen atom, the at least one protic ammonium cation acting to react with a target gas via deprotonation.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DESCRIPTION OF EMBODIMENTS

It will be readily understood that the components of the embodiments of the invention, as generally described and illustrated in the figures herein, may be arranged and designed in a wide variety of different configurations in addition to the described exemplary embodiments. Thus, the following more detailed description of the embodiments of the invention, as represented in the figures, is not intended to limit the scope of the embodiments of the invention, as claimed, but is merely representative of exemplary embodiments of the invention.

Reference throughout this specification to "one embodiment" or "an embodiment" (or the like) means that a particular feature, structure, or characteristic described in connection with the embodiment is included in at least one embodiment of the invention. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in at least one embodiment. In the following description, numerous specific details are provided to give a thorough understanding of embodiments of the invention. One skilled in the relevant art will recognize, however, that the various embodiments of the invention can be practiced without at least one of the specific details, or with other methods, components, materials, et cetera. In other instances, well-known structures, materials, or operations are not shown or described in detail to avoid obscuring aspects of the invention.

The description now turns to the figures. The illustrated embodiments of the invention will be best understood by reference to the figures. The following description is intended only by way of example and simply illustrates certain selected exemplary embodiments of the invention as claimed herein.

Figure 1:
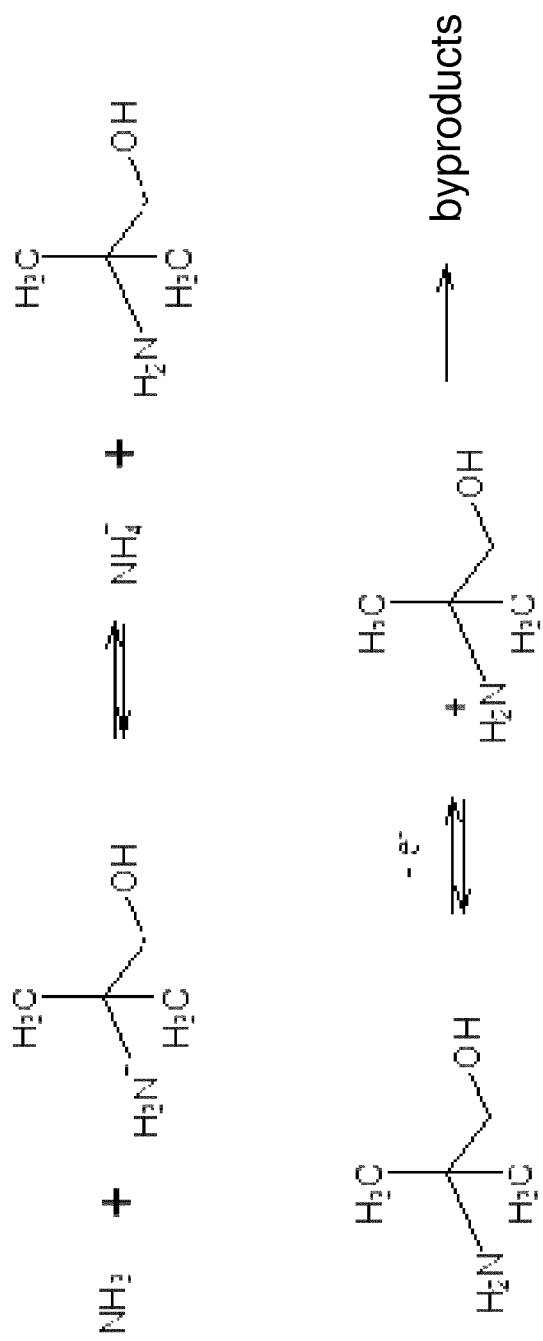
FIG. 1 sets forth equations relating to a measurement principle for ammonia detection.
Figure 2:
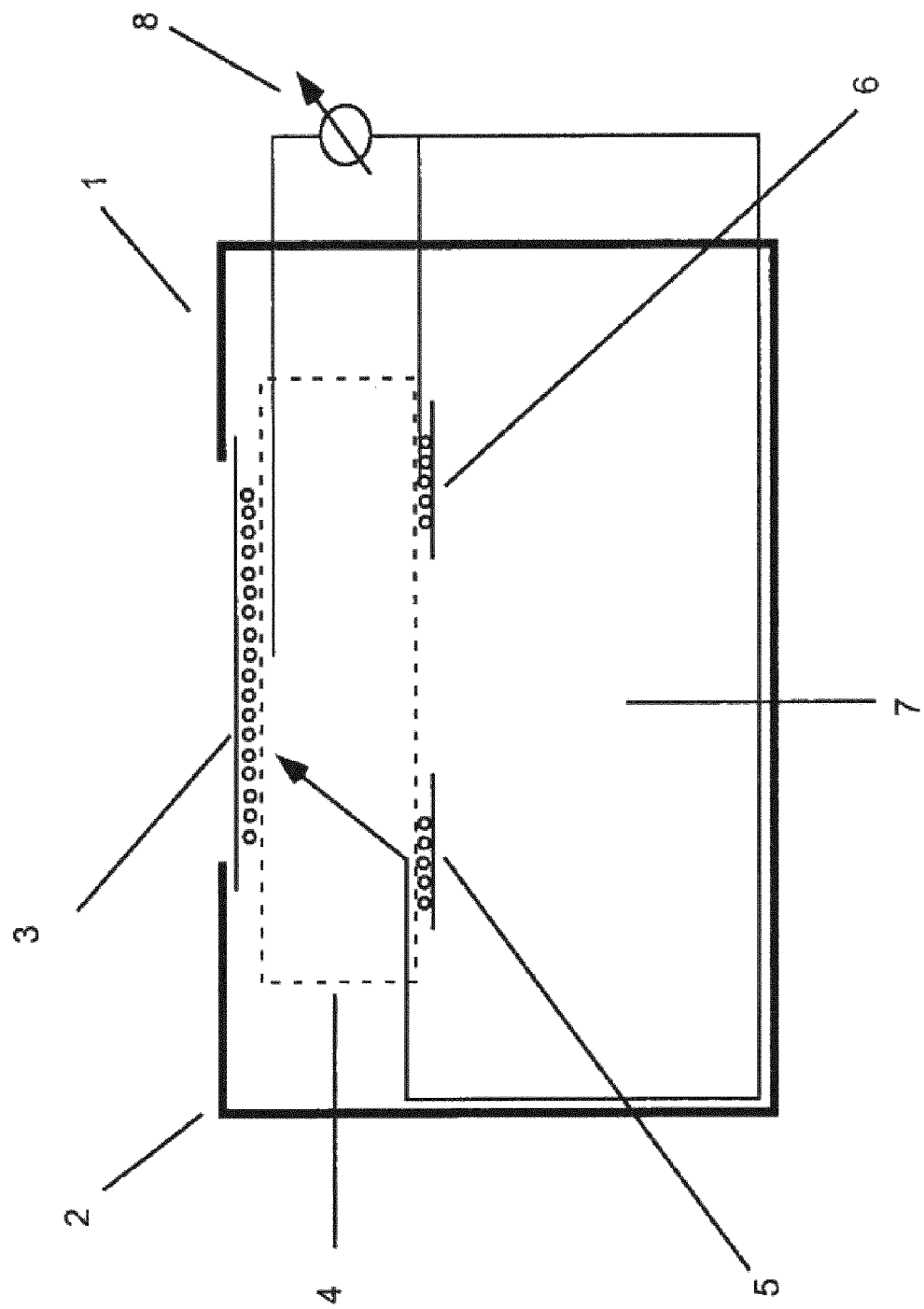
FIG. 2 schematically illustrates a first variant of an electrochemical three-electrode gas sensor.
Figure 3:
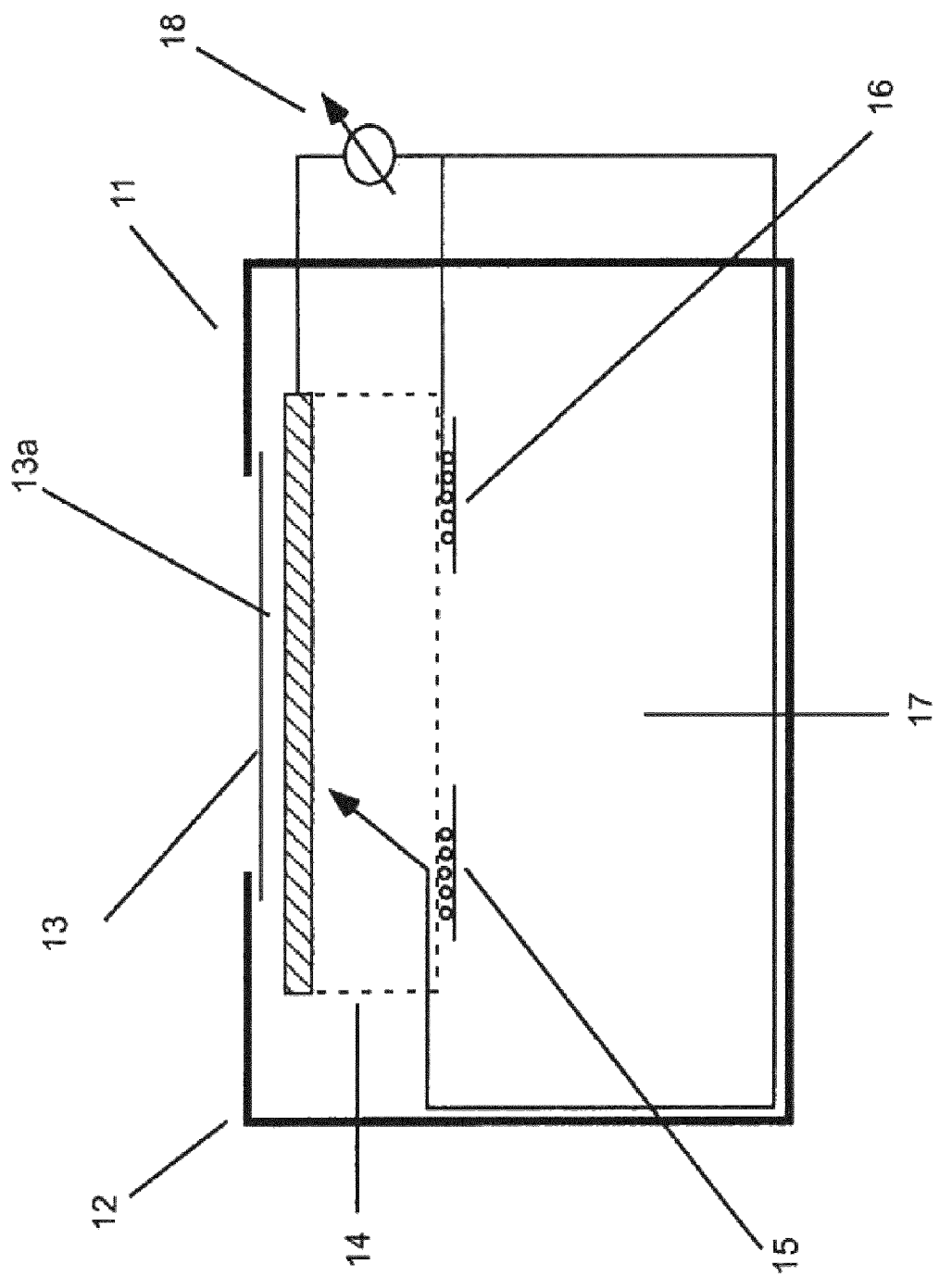
FIG. 3 schematically illustrates a second variant of an electrochemical three-electrode gas sensor.
Figure 4:
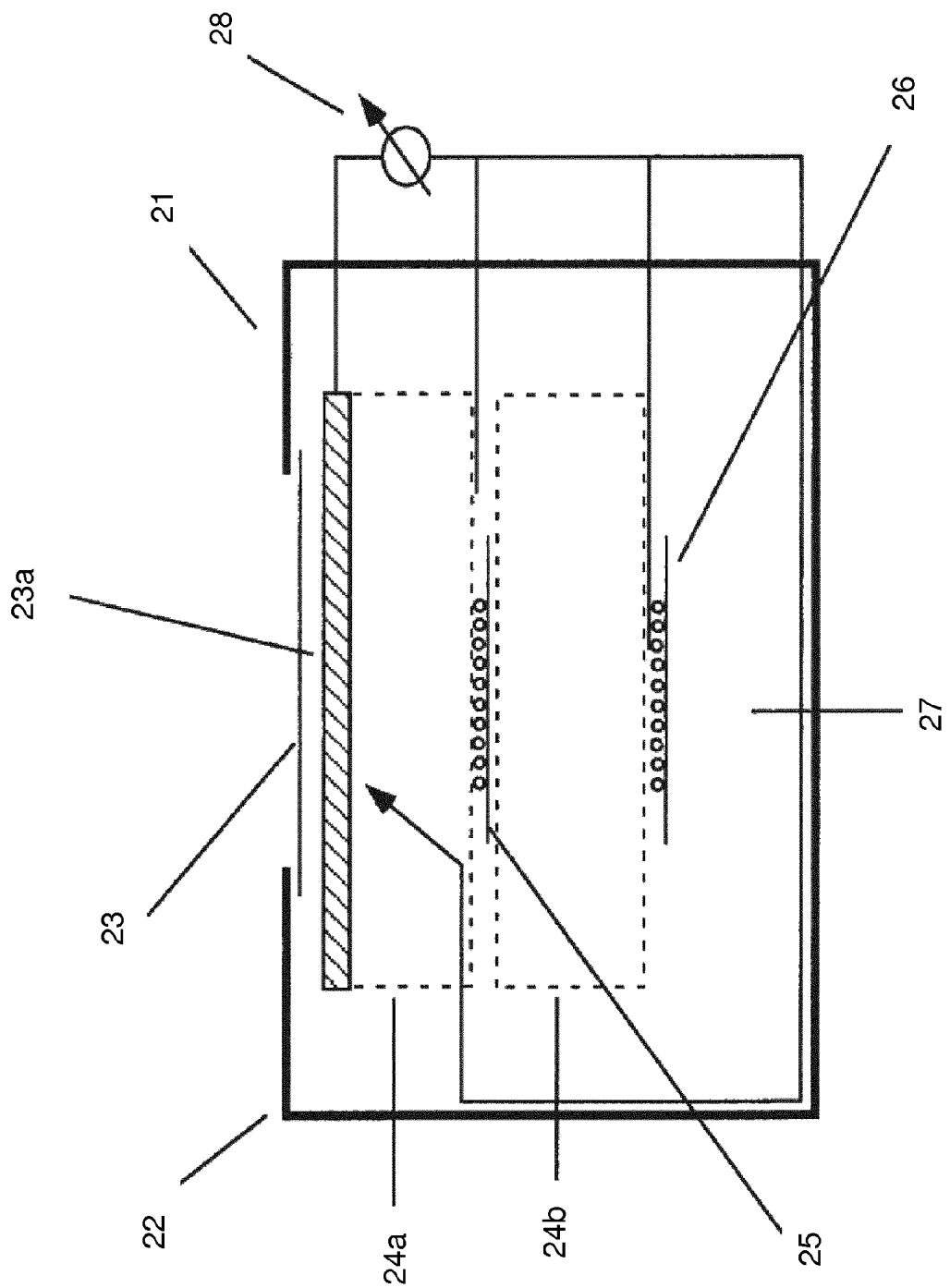
FIG. 4 schematically illustrates a third variant of an electrochemical three-electrode gas sensor.

To facilitate easier reference, in advancing from FIG. 2 to and through FIG. 4, a reference numeral is advanced by a multiple of 10 in indicating a substantially similar or analogous component or element with respect to at least one component or element found in at least one earlier figure among FIGS. 2-4.

Broadly contemplated herein, in accordance with at least one embodiment of the invention, there is provided an electrochemical gas sensor, particularly for measuring ammonia and amines, that shows high stability even in the presence of high gas concentrations and that is suitable for miniaturization. Accordingly, an electrochemical gas sensor is availed, particularly for the detection of ammonia and amines, with an ionic liquid as an electrolyte. The ionic liquid that is employed includes at least one protic ammonium cation with at least one dissociable, i.e., separable hydrogen atom, wherein at least one ammonium cation reacts, via deprotonation, with the ammonia and amines to be measured.

It is to be understood that the term "dissociable" within the context of the present invention relates to a heterolytical dissociation, i.e the reversible decomposition into a cation and anion. Homolytic cleavages providing radicals do not fall under this definition.

In accordance with at least one embodiment of the invention, the ammonium cation of the ionic liquid used in a gas sensor so reacts with ammonia and/or amines via the following general equation (as an example):

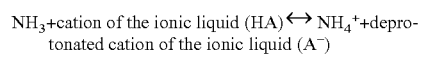

The fundamental property of the ionic liquid used in a gas sensor is the capability of the corresponding cation of the ionic liquid to react with the target gas, such as ammonia, in an acid-base reaction.

This in turns means that not all ammonium cations having a free proton are able to undergo such a reaction. Rather only specific ammonium cations which are able to release a proton in the presence of ammonia and/or amines and are thus acidic enough to transfer the proton to ammonia and/or amines are suitable for solving the object of the present invention. If for instance the proton is bound to a N-atom being part of a conjugated system such as in guanidinium-cation (with a pKa value of 13.6) then the proton does not dissociate from the ammonium cation and can thus not react with ammonia and/or an amine. Thus, the protic ammonium cation applied in the present invention is not based or part of an electron conjugated system. Ammonium cations based on alkylated amines having no functional substituents such as ethylammonium cation (with a pKa value of 10.8) are not favourable for the present invention since these cations are not easily deprotonated by the target gas and are thus not able to release a proton in presence of ammonia or amines in a desired manner.

In accordance with at least one embodiment of the invention, in contrast to inert cations of ionic liquids as known, the free bases of the cation, arising from deprotonation with ammonia, can be oxidized at the measurement electrode of the gas sensor. The oxidation of this free base, as opposed to a direct oxidation of ammonia, provides reduced deviation and drift of the sensor signal, since diverse products are formed in this reaction. Furthermore, the oxidation of the free base of the cation of the ionic liquid might occur at a lower potential, thereby permitting a concerted the use of less active catalysts, thus increasing the selectivity of the sensor.

In accordance with at least one embodiment of the invention, and preferably, as shown in the above equation, the ammonium cation of the ionic liquid reacts directly, that is, in a direct fashion without an intermediary reactant with the ammonia and/or amines and via deprotonation. However, it is also possible for the reaction between the ammonium cation of the ionic liquid and the ammonia and/or amines to be measured not to be direct, but to be carried out via a mediator. Such a mediator works in the manner of an intermediary reactant between ammonium cation and ammonia/amine.

By way of example in accordance with at least one embodiment of the invention, water can be considered as an intermediary reactant, or mediator. At a high ambient humidity, it is absorbed by the ionic liquid. Depending on the nature of the ionic liquid, it might take up significant amounts of water. In the presence of ammonia, water reacts in accordance with this equation:

$$NH_3 + H_2O \rightarrow OH^- + NH_4^+$$

In turn, the hydroxide ions so formed react with the ammonium cation of the ionic liquid in accordance with this equation:

$$OH^- + \text{cation of ionic liquid (HA)} \leftrightarrow H_2O + \text{deprotonated cation of ionic liquid (A}^-\text{)}$$

Subsequently, the free base of the cation of the ionic liquid is oxidized at the measurement electrode of the gas sensor, e.g., as described hereabove.

In accordance with at least one embodiment of the invention, a variety of other mediators or intermediary reactants are conceivable besides water.

In general, in accordance with at least one embodiment of the invention, it can be said that in the particular case of choosing an ionic liquid, the type of possible mediator and its concentration, as well as other external conditions, depends on whether a direct reaction between an ammonium cation of the ionic liquid and ammonia is being addressed or if mediators are to serve a purpose.

In accordance with at least one embodiment of the invention, it is preferable for the pKa value of the ammonium cation to be less than about 9.25. In the context of the present invention, the pKa value constitutes the negative common logarithm of the acid dissociation constant Ks or Ka. The acid dissociation constant Ks or Ka is a substance constant and conveys the extent to which a substance reacts in an equilibrium reaction with a solvent under protolysis, per this equation:

$$HA + Y \leftrightarrow HY^+ + A^-$$

Here, HA represents an acid, such as a Brønsted acid, that can emit $H^+$ to a solvent Y, such as water. As a result of this reaction, there are formed a protonated solvent $HY^+$ and an anion $A^-$. Ks or Ka is thence the equilibrium constant of this reaction and, as such, a measure of the strength of an acid. The stronger an acid is, the more the reaction shifts to the right-hand side, that is, the higher the concentrations of $H^+$ and $A^-$ will be. The equilibrium constant will now be given as a negative common logarithm in the form of a pKs or pKa value. This means that the smaller the pKs value, the stronger the acid.

As such, in accordance with at least one embodiment of the invention, it can be appreciated that a pKa value of 9.25 corresponds to the pKa value of ammonium ions when water is used as a solvent. The use of an ionic liquid with ammonium cations with a pKa value of less than 9.25 is desirable to shift the dissoziation equilibrium of the reaction of ammonia as a solvent onto the side of ammonium ions.

As well as detecting ammonia, a gas sensor in accordance with at least one embodiment of the invention can also be used for measuring amines, particularly gaseous amines such as methylamine or ethylamine.

In accordance with at least one embodiment of the invention, in a gas sensor for detecting ammonia and amines, the at least one ammonium cation of the ionic liquid is selected from the group comprising: a monosubstituted ammonium cation, a disubstituted ammonium cation and a trisubstituted ammonium cation.

Thus, the at least one ammonium cation of the ionic liquid relates to the general formula $$[NH_x(R_{1m}R_{2n}R_{3o})]^+$$

Wherein x=1, 2 or 3; m=n=o=0, 1, 2 or 3 with (m+n+o)=1, 2 or 3, and

Wherein $R_1$, $R_2$ and $R_3$ are in each case a substituent with an electron withdrawing group, preferably an alkyl, aryl or heteroaryl group with at least one electron withdrawing group or moiety as defined in detail below, and Wherein $R_1$, $R_2$ and $R_3$ can be the same or different.

It is also to be understood within the context of the present invention that the nitrogen atom of the ammonium cation is preferably not part of an aromatic ring system such as for instance in pyridine or imidazol. Thus, heteroaromatic systems comprising an ammonium cation are exempted as part of the N in the above general formula. However, any of the substituents $R_1$, $R_2$ or $R_3$ may comprise heteroaromatic systems, but in this case the N atom forming the ammonium cation is not part of said heteroaromatic system. It is to be understood that the ammonium cation is preferably not part of a mesomerism stabilized or conjugated system. It may also of an advantage if the ammonium cation is chosen such that pyridin and imidazol are exempted.

In an electron withdrawing group, in accordance with at least one embodiment of the invention, groups and substituents are understood to portray a negative inductive effect (that is, −I-effect) and thereby reduce the electron density in the local environment. The reduction in electron density at a carbon atom or at other heteroatom also has an effect on the reactivity of the hydrogen atoms adhering to the carbon atom or heteroatom. This arises from the fact that the carbon atom or heteroatoms attempts to compensate for lacking electron density in such a way that it draws in closer the bonding electrons of the CH-/Heteroatom-H bonds. This leads to a loosening of the binding of H-atoms and thus increases the acidity of the H atoms. In the case of embodiments of the present invention, there is thus facilitated, for the use of substituents with at least one electron withdrawing group on the ammonium cation, an easier separation of the hydrogen atom, and thus a shift in the acid-base equilibrium reaction, in accordance with the above equation, in the direction of ammonium ions and free base.

In accordance with at least one embodiment of the present invention, the ammonium cation includes at least one substituent with at least one electron withdrawing group, wherein the latter is selected from a group comprising: branched or unbranched C1-C20 alkyl groups, preferably C1-C10 alkyl groups, particularly preferably C1-C5 alkyl groups. It is in general also possible that the at least one substituent is an aryl or heteroaryl group. These alkyl, aryl and/or heteroaryl-groups end up being substituted with at least one electron withdrawing group.

It is hence preferred, in accordance with at least one embodiment of the invention, that the at least one branched or unbranched alkyl group, aryl or heteroaryl group, in particular C6-C10 aryl or heteroaryl groups, include the electron withdrawing group at the C1, C2 or C3 atom of the group, preferably at the C1 and/or C2 atom of the alkyl group or in any position of the aromatic or heteroaromatic system. The numbering of the carbon atoms of the alkyl group at hand, using C1, C2 or C3, starts from the heteroatom nitrogen. In other words, the carbon atom of the linked group used as a substituent, and that occurs as the first or nearest carbon atom with respect to the nitrogen atom of the ammonium cation, is designated as C1 in the context of embodiments of the present invention. The numbering of the other carbon atoms continues as per this scheme.

In a particularly preferred embodiment of the invention, the at least one electron withdrawing group is selected from a group comprising: OH, halogen, cyano, isocyano, halogen-substituted alkyl, especially halogen-substituted methyl group, thiocyano, isothiocyano, primary, secondary or tertiary amine, azide, thiol, alkoxy and cycloalkoxy, preferably HO-, F-substituted and unsubstituted $C_1$-$C_{12}$-Alkoxy. As well, these can be used as suitable electron withdrawing groups: trifluoromethanesulfonate, monofluorobutane-sulfonate, para-toluoylsulfonate p-Brombenzonsulfonate, p-nitrobenzenesulfonate, methanesulfonate or 2,2,2-trifluoroethanesulfonate. For a particular advantage, the electron withdrawing groups can be selected from the group comprising: OH, halogen, methyl group substituted with halogen, such as a mono-, di- or trisubstituted methyl group, wherein the halogen trisubstituted methyl group is mostly preferred, and cyano.

Particularly suitable ammonium cations, in the context of at least one embodiment of the invention, include: di(2-hydroxyethyl)ammonium cation, (2-trifluoroethyl)-ammonium cation and/or di(cyanomethyl)ammonium cation. Anions employed in the ionic liquid can preferably be selected from this group: nitrates, nitrites, trifluoroacetates, tetrafluoroborates, hexafluorophosphates, polyfluoralkanesulfonate, bis(trifluoromethylsulfonyl)imide, alkyl sulfates, alkane sulfonates, acetates and the anions of fluorinated alkanoic acids.

Preferably, in accordance with at least one embodiment of the invention, ionic liquids used in an electrochemical gas sensor, particularly for the detection of ammonia and amines, can include: di(2-hydroxyethyl)ammonium trifluoracetate, (2-trifluoroethyl)ammonium nitrate and/or di(cyanomethyl) ammonium nitrate.

Generally, in accordance with at least one embodiment of the invention, it is also possible to employ mixtures of different ionic liquids. A mixture of different ionic liquids is then advantageous if different polarities are to be accommodated in the electrolyte and if, for instance, certain additives need to be released or the water absorption of the electrolyte needs to be controlled.

In an electrochemical gas sensor in accordance with at least one embodiment of the invention, the ionic liquid used as an electrolyte can be absorbed in a solid the form of a powder and/or fibrous solid based on silicon dioxide, or not be absorbed in a solid. If the electrolyte is absorbed in a powder and/or interwoven fibrous solid based on silicon dioxide, then a solid-state electrolyte comes to be formed in the gas sensor. In such a solid-state electrolyte, the electrodes of the gas sensor are preferably applied to a gas permeable membrane or, in the powder form, are mixed directly with the electrolyte.

Preferably, the powdered solid based on silicon dioxide is a silicate with an average particle size of at least 5 µm, preferably at least 50 µm, particularly preferably at least 75 µm. The solid based on silicon dioxide preferably has a specific surface area of at least 50 $m^2$/g, preferably at least 100 $m^2$/g, most preferably at least 150 $m^2$/g, and has a silicon dioxide content of at least 95 wt %. Preferably, for the solid at hand, a pure silicon dioxide or aluminum or calcium silicate is used. Especially preferred is a silicate with an average particle size of 100 µm, a specific surface area of 190 $m^2$/g, and a silicon dioxide content of at least 98 wt %.

In at one embodiment of the invention, an electrochemical gas sensor includes at least two electrodes that are in electrical contact with the ionic liquid and are electrically isolated from each other. This can be brought about, for instance, by suitable separation elements or by an adequate separation distance. Two-electrode arrangements, that is, a working electrode and a counter electrode, or three-electrode arrangements, that is, a working electrode, a counter electrode and a reference electrode, are preferably employed. Generally, it is also possible to use additional electrodes, such as a cover or protective electrode or more measurement electrodes in the form of a multi-electrode system. The electrodes are preferably formed from a metal from the group comprising: Cu, Ni, Ti, Pt, Ir, Au, Pd, Ag, Ru, and Rh, their mixtures, and/or their oxides or carbons (e.g., in the form of carbon nanotubes, graphene, diamond-like carbon or graphite), whereby the electrodes can be formed from the same or different materials. The electrodes can each take on an appropriate structure for the sensor construction employed.

In further embodiments of the invention, organic and/or metal-organic and/or inorganic additives or additive portions are added to the ionic liquid used as an electrolyte. Said additive portions are present in an amount between about 0.05 and about 1 wt %. These additives particularly serve to improve the sensitivity, selectivity and robustness of the sensors. The additives can be included at 0.05 to 1.5 wt % for organic additives, at 1 to 12 wt % for inorganic additives and at 0.05 to 1 wt % for metal-organic additives.

In that connection, the organic additives of the ionic liquid are preferably selected from a group comprising: imidazole, pyridine, pyrrole, pyrazole, pyrimidine, guanine, unsubstituted or substituted with at least one C1-C4 alkyl group, uric acid, benzoic acid and porphyrins and their derivatives. A derivative within the meaning of the present invention is compound having a similar structure derived from a corresponding basic compound. Derivatives are usually compounds in which H-atoms or other groups are replaced by another atom or atom group or in which one or multiple atoms or atom groups are removed.

The metal-organic additives are preferably selected from a group comprising: metal-organic phthalocyanines and their derivatives, whereby the metal cation of the phthalocyanine is preferably $Mn^{2+}$, $Cu^{2+}$, $Fe^{2+}$, $Fe^{3+}$ or $Pb^{2+}$.

The inorganic additives are preferably selected from a group comprising: alkali halides and ammonium halides, which are unsubstituted or substituted by C1-C4 alkyl, as well as transition metal salts from the group $Mn^{2+}$, $Mn^{3+}$, $Cu^{2+}$, $Ag^+$, $Cr^{3+}$, $Cr^{6+}$, $Fe^{2+}$, $Fe^{3+}$, and lead salts. Preferably, the inorganic additives are selected from this group: lithium bromide, lithium iodide, ammonium iodide, tetramethylammonium iodide, tetraethylammonium iodide, tetrapropylammonium iodide, tetrabutylammonium iodide, tetrabutylammonium bromide, manganese (II) chloride, manganese (II) sulfate, manganese (II) nitrate, chromium (III) chloride, alkali chromate, iron (II) chloride, iron (III) chloride and lead (II) nitrate.

In accordance with at least one embodiment of the invention, the additives discussed above may also be used in mixtures. This can encompass mixtures of different additives in the same group, for instance mixtures of various organic additives, as well as mixtures of different additives, for instance mixtures of, e.g., of organic and inorganic additives. Through the use of mixtures of different additives it is possible to customize the sensitivity of the sensors towards specific requirements.

In accordance with at least one embodiment of the invention, a gas sensor for the detection of ammonia and amines functions as a second-order head in the classical sense of a Clark cell with precious metal catalysts and carbon used as the measurement and counter electrodes in a two-electrode system, or with an additional electrode in a three-electrode operation. The operation of such a gas sensor is thus amperometric, while modes of operation or working other than amperometric are generally possible.

As described hereinabove, in accordance with at least one embodiment of the invention, an ionic liquid can end up being absorbed by a solid based on silicon dioxide. In such an embodiment, the solid appears in the sensor as a filling or layering, or is in pressed form. A filling or layering permits a very flexible design of the sensors. Pressing the solid into pellet form is also possible.

Preferably, in accordance with at least one embodiment of the invention, and as indicated hereinabove, the electrochemical gas sensor is used for amperometric measurements. This relates particularly to a gas sensor with an unabsorbed arrangement of ionic fluids with and without additives, and the variant of a solid state electrolyte with ionic liquids (with or without additives).

In accordance with at least one embodiment of the invention, FIG. 2 shows a gas sensor 1 that includes a sensor housing 2, within which are disposed a measurement electrode 3, a working electrode 5 and a counter electrode 6. The measurement electrode 3 is in communication with ambient via a gas-permeable membrane. The electrodes are separated from one another by a separator 4, which is formed from glass fibers or silica structures and is saturated with electrolyte. In the present example, the electrolyte is an ionic liquid containing a protic ammonium cation. In a rear space of the sensor, a compensating volume 7 is afforded, where water can be accommodated during atmospheric humidity fluctuations. The sensor is connected to measurement electronics 8, which amplify the sensor current into a measurement signal in the presence of the target gas, in this case ammonia or amines.

In accordance with at least one other embodiment of the invention, FIG. 3 shows a gas sensor 11 that includes a sensor housing 12, within which are disposed a measurement electrode 13a, working electrode 15 and counter electrode 16. Here, as well, the measurement electrode 13a is in communication with the atmosphere via a gas permeable membrane 13. The measurement electrode 13a is comprised of a layer with catalyzer/electrode material and electrolyte. In the present example, the electrolyte is embodied by ionic fluid with at least one protic ammonium cation which is capable of reacting with the ammonia or amines to be measured. The ionic liquid can be absorbed by a powdered solid based on silicon dioxide. The individual electrodes are separated from one another via a separator 14, itself formed from glass fibers or silica structures. The working electrode 15 and counter electrode 16 are each positioned adjacent one another at the side of the measurement electrode 13a opposite the separator 14. Also provided here, in a rear space of the sensor, is a compensating volume 17, for accommodating water during atmospheric humidity fluctuations. The sensor is connected to measurement electronics 18 which, on the one hand, provides a stable and adjustable potential at the working electrode and, on the other hand, provides output information to other devices.

In accordance with at least yet another embodiment of the invention, FIG. 4 shows a gas sensor 21 that includes a sensor housing 22, within which are disposed a measurement electrode 23a, working electrode 25 and counter electrode 26. In this embodiment, as well, the measurement electrode 23a is in communication with the environmental atmosphere via a gas permeable membrane 23. The measurement electrode 23a is comprised of a layer with catalyzer/electrode material and electrolyte. In the present example, the electrolyte is the ionic fluid containing at least one protic ammonium cation according to the present invention, which is absorbed by a powdered solid based on silicon dioxide. The measurement electrode 23a and working electrode 25 are in ionic condictive contact with one another via a first separator 24a formed from glass fibers or silica structures that is saturated with ionic electrolytes according to the invention. Further, the working electrode 25 and counter electrode 26 are in ionic condictive contact via a second separator 24b. The counter electrode 26 is thereby positioned at that side of the second separator 24b which is away from or opposite the working electrode 25. In other words, in the present embodiment of a gas sensor, the measurement electrode 23a, working electrode 25 and counter electrode 26 are positioned in a stack. In a rear space of the sensor, a compensating volume 27 serves to accommodate water during atmospheric humidity fluctuations. The sensor is again connected to measurement electronics 28.

In a working example, in accordance with at least one embodiment of the invention, a gas sensor is used with a structure analogous to that of the embodiment of FIG. 2. Particularly, the sensor used in the present example comprises a measurement electrode, a counter electrode and working electrode, in which each electrode included iridium. Electrolyte-saturated separators are positioned between the electrodes to ensure ionic conductivity between the individual electrodes and to prevent short circuiting between the electrodes.

Figure 5:
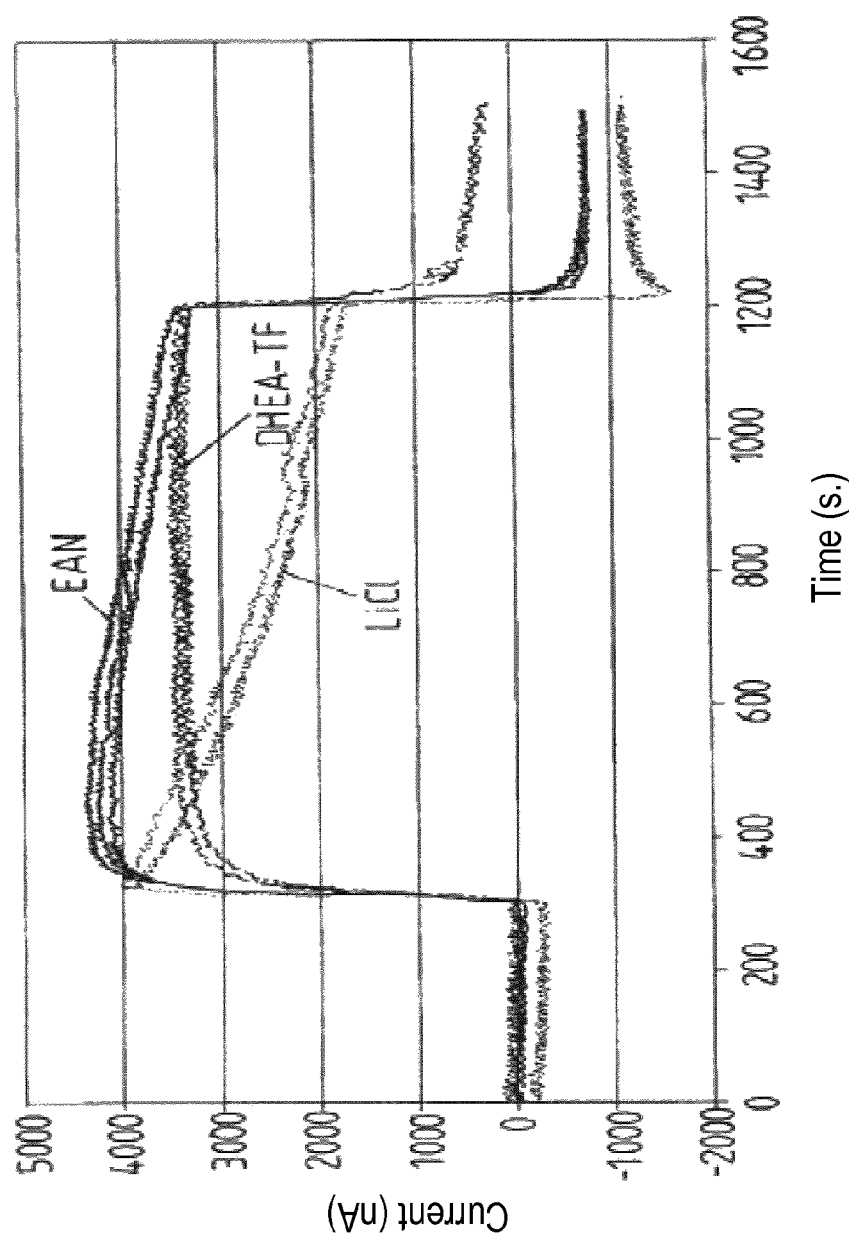
FIG. 5 graphically illustrates the sensor function of three $NH_3$ gas sensors, each containing a different electrolyte.

In experimentation, in accordance with the present working example in accordance with at least one embodiment of the invention, three different electrolytes were investigated for their capability to be used in an ammonia gas sensor. The behavior of lithium chloride LiCl as an aqueous electrolyte (see chart in FIG. 5) was compared to that of the ionic liquid ethylammonium EAN and the (2-hydroxyethyl)-TF ammoniumtrifluoroacetate DHEA. As can be seen from FIG. 5, signal stability increases when DHEA-TFH (containing a protic ammonium cation of the present invention) is used, as compared to the aqueous lithium chloride electrolyte solution and also to the ionic liquid ethylammonium nitrate (which itself already offers an increase in stability of an ammonia gas sensor).

As can be seen in accordance with the present working example (in accordance with at least one embodiment of the invention), the stability of the ammonia gas sensor enhanced with the ionic liquid DHEA-TFA has a pKa value of 8.88, while that of the ionic liquid ethylammonium nitrate is 10.81. Since the stability of the gas sensor using DHEA-TFH as compared to that with ethylammonium nitrate is significantly increased (see FIG. 5), the impact and importance of the pKa value of the ionic liquid is apparent. Thus, it can be concluded that the use of functionalized ionic liquids containing ammonium cations with at least one removable hydrogen atom, particularly ammonium cations, which are substituted with at least one electron withdrawing group, are suitable to improve the signal stability of ammonia gas sensors significantly.

This disclosure has been presented for purposes of illustration and description but is not intended to be exhaustive or limiting. Many modifications and variations will be apparent to those of ordinary skill in the art. The embodiments were chosen and described in order to explain principles and practical application, and to enable others of ordinary skill in the art to understand the disclosure for various embodiments with various modifications as are suited to the particular use contemplated.

Although illustrative embodiments of the invention have been described herein with reference to the accompanying drawings, it is to be understood that the embodiments of the invention are not limited to those precise embodiments, and that various other changes and modifications may be affected therein by one skilled in the art without departing from the scope or spirit of the disclosure.

What is claimed is:

1. An electrochemical gas sensor comprising:
an electrolyte comprising an ionic liquid;
said ionic liquid including at least one protic ammonium cation with at least one dissociable hydrogen atom, said at least one protic ammonium cation acting to react with a target gas via deprotonation;
wherein said at least one protic ammonium cation has a pKa value of less than about 9.25.

2. The gas sensor according to claim 1, wherein the target gas comprises at least one taken from the group consisting of: ammonia and amines.

3. The gas sensor according to claim 1, wherein said gas sensor is configured for detecting at least one target gas selected from the group consisting of ammonia and amines.

4. The gas sensor according to claim 1, wherein said at least one protic ammonium cation is selected from the group consisting of: a monosubstituted ammonium cation; a disubstituted ammonium cation; and a trisubstituted ammonium cation.

5. The gas sensor according to claim 1, wherein said at least one protic ammonium cation includes at least one substituent having at least one electron withdrawing group.

6. The gas sensor according to claim 5, wherein said at least one substituent having at least one electron withdrawing group comprises at least one alkyl group selected from the group consisting of: branched C1-C20 alkyl groups; and unbranched C1-C20 alkyl groups; at least one aryl and/or at least one heteroaryl group.

7. The gas sensor according to claim 6, wherein said at least one alkyl, aryl and/or heteroaryl group is substituted with at least one electron withdrawing group at the C1 atom; at the C2 atom; or at the C3 atom of the at least one alkyl, aryl or heteroaryl group, or at any other position of the aryl and/or heteroaryl group.

8. The gas sensor according to claim 5, wherein said at least one substituent having at least one electron withdrawing group comprises at least one C1-C10 alkyl group substituted with at least one electron withdrawing group.

9. The gas sensor according to claim 5, wherein said at least one electron withdrawing group is selected from the group consisting of: OH; halogen; cyano; isocyano; halogen substituted alkyl; in particular halogen-substituted methyl group; thiocyano; isothiocyano; amine; azide; thiol; alkoxy; cycloalkoxy; HO-substituted, F-substituted and unsubstituted $C_1$-$C_{12}$-alkoxy; trifluoromethanesulfonate (triflate); nonafluorobutanesulfonate (nonaflate); p-toluoylsulfonate (tosylate); p-Brombenzonsulfonate (brosylate); p-nitrobenzenesulfonate (tosylate); methanesulfonate (mesylate); and 2,2,2-Trifluoroethanesulfonate (tresylate).

10. The gas sensor according to claim 5, wherein said at least one electron withdrawing group is selected from the group consisting of: OH; halogen; methyl group substituted with at least one halogen, in particular methyl group trisubstituted with halogen; and cyano.

11. The gas sensor according to claim 1, wherein said at least one protic ammonium cation is selected from the group consisting of: di(2-hydroxyethyl)ammonium; (2-trifluoroethyl)-ammonium; and di(cyanomethyl)ammonium.

12. The gas sensor according to claim 1, wherein the amonium cation is not part of a heteroaromatic ring system.

13. The gas sensor according to claim 1, wherein said ionic liquid comprises at least one anion selected from the group consisting of: nitrates; nitrites; trifluoroacetates; tetrafluoroborates; hexafluorophosphates; polyfluoralkanesulfonates; bis(trifluoromethylsulfonyl)imide; alkyl sulfates; alkane sulfonates; acetates; and anions of fluorinated alkanoic acids.

14. The gas sensor according to claim 1, wherein said ionic liquid comprises at least one selected from the group consisting of di(2-hydroxyethyl) ammonium trifluooracetate; (2-trifluoroethyl) ammonium nitrate; and di(cyanomethyl)ammonium nitrate.

15. The gas sensor according to claim 1, wherein said electrolyte is absorbed in a solid.

16. The gas sensor according to claim 15, wherein said solid comprises at least one solid selected from the group consisting of: $SiO_2$-based solid in powder form; and $SiO_2$-based solid in fibrous form.

17. The gas sensor according to claim 1, further comprising at least two electrodes in electrical contact with said electrolyte and in electrical isolation from each other.

18. The gas sensor according to claim 17, wherein said electrodes are each formed from at least one metal selected from the group consisting of: Cu; Ni; Ti; Pt; Ir; Au; Pd; Ag; Ru; Rh; their mixtures; their oxides; and carbons.

19. The gas sensor according to claim 1, wherein said electrolyte further comprises an additive portion comprising at least one additive selected from the group consisting of: organic additives; metal-organic additives; and inorganic additives.

20. The gas sensor according to claim 19, wherein the additive portion is present in an amount between about 0.05 and about 15 wt % of the total weight of the electrolyte.

21. The gas sensor according to claim 19, wherein organic additives, when present, are present in an amount between about 0.05 and about 1.5 wt %; inorganic additives, when present, are present in an amount between about 1 and about 12 wt %; and metal-organic additives, when present, are present in an amount between about 0.05 and about 1 wt %.

22. The gas sensor according to claim 1; wherein said electrolyte includes at least one organic additive selected from the group consisting of: imidazole; pyridine; pyrrole; pyrazole; pyrimidine; guanine; uric acid; benzoic acid; porphyrins; and their derivatives.

23. The gas sensor according to claim 1, wherein said electrolyte includes at least one metal-organic additives selected from the group consisting of: metal-organic phthalocyanines; and derivatives of metal-organic phthalocyanines; wherein a metal cation of the metal-organic phthalocyanine or the metal-organic phthalocyanine derivative is selected from the group consisting of $Mn^{2+}$, $Cu^{2+}$, $Fe^{2+}$, $Fe^{3+}$, and $Pb^{2+}$.

24. The gas sensor according to claim 1, wherein said electrolyte includes at least one inorganic additive selected from the group consisting of: alkali halides; ammonium halides; a transition metal salt selected from the group consisting of $Mn^{2+}$, $Mn^{3+}$, $Cu^{2+}$, $Ag^+$, $Cr^{3+}$, $Cr^{6+}$, $Fe^{2+}$, and $Fe^{3+}$, and lead salts.

\* \* \* \* \*